US009060447B2

(12) United States Patent
Hino et al.

(10) Patent No.: US 9,060,447 B2
(45) Date of Patent: Jun. 16, 2015

(54) SUBSTRATE STRUCTURE

(71) Applicant: Olympus Medical Systems Corp., Tokyo (JP)

(72) Inventors: Kazuhiko Hino, Hachioji (JP); Takafumi Kubo, Akiruno (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 14/338,865

(22) Filed: Jul. 23, 2014

(65) Prior Publication Data
US 2014/0367159 A1    Dec. 18, 2014

Related U.S. Application Data

(63) Continuation of application No. PCT/JP2013/078432, filed on Oct. 21, 2013.

(30) Foreign Application Priority Data

Nov. 29, 2012    (JP) .................................. 2012-261195

(51) Int. Cl.
| | |
|---|---|
| *H05K 1/18* | (2006.01) |
| *A61B 1/05* | (2006.01) |
| *H05K 9/00* | (2006.01) |
| *G02B 23/24* | (2006.01) |

(52) U.S. Cl.
CPC ............ *H05K 1/184* (2013.01); *G02B 23/2476* (2013.01); *A61B 1/051* (2013.01); *H05K 9/00* (2013.01); *H05K 2201/10287* (2013.01); *H05K 2201/2036* (2013.01)

(58) Field of Classification Search
CPC . H05K 1/184; H05K 9/00; H05K 2201/2036; H05K 2201/10287; H05K 1/14; H05K 1/144; A61B 1/051; G02B 23/2476
USPC .......................................... 174/360, 255, 261
See application file for complete search history.

(56) References Cited

U.S. PATENT DOCUMENTS 5,298,684 A * 3/1994 Leeb ............................. 174/250
5,375,322 A   12/1994 Leeb
(Continued)

FOREIGN PATENT DOCUMENTS

| EP | 2157838 A1 | 2/2010 |
|---|---|---|
| JP | 05-075313 A | 3/1993 |

(Continued)

*Primary Examiner* — Hoa C Nguyen
*Assistant Examiner* — Amol Patel
(74) *Attorney, Agent, or Firm* — Scully, Scott, Murphy & Presser, P.C.

(57) ABSTRACT

A substrate structure includes: a first substrate; a second substrate including a front face disposed so as to face a front face of the first substrate, a substrate spacing holding member provided between the front faces of the substrates facing each other, and holds a spacing between the two substrates at a predetermined value; a mounted component including a signal wire mounted on the second substrate, the signal wire, including an end portion electrically connected to the second substrate and extending from the substrate to an outside along the front face of the second substrate; a through hole provided in the first substrate, the through disposing a projecting part of the mounted component therein; and a shielding member being provided on a back face side of the first substrate and covering an entirety or at least a part of an opening of the through hole.

5 Claims, 6 Drawing Sheets

(56) References Cited

U.S. PATENT DOCUMENTS

| | | |
|---|---|---|
| 5,476,970 A | 12/1995 | Rains et al. |
| 2010/0170700 A1* | 7/2010 | Nakamura et al. ............ 174/254 |

FOREIGN PATENT DOCUMENTS

| | | |
|---|---|---|
| JP | 6-501137 A | 2/1994 |
| JP | 08-172303 A | 7/1996 |
| JP | 3002539 B2 | 1/2000 |
| JP | 2009-038361 A | 2/2009 |
| JP | 2009-158606 A | 7/2009 |
| JP | 2009-206302 A | 9/2009 |
| JP | 2010-072272 A | 4/2010 |
| WO | WO 92/22995 A1 | 12/1992 |
| WO | WO 2008149511 A1 | 12/2008 |

* cited by examiner

SUBSTRATE STRUCTURE

CROSS REFERENCE TO RELATED APPLICATION

This application is a continuation application of PCT/JP2013/078432 filed on Oct. 21, 2013 and claims benefit of Japanese Application No. 2012-261195 filed in Japan on Nov. 29, 2012, the entire contents of which are incorporated herein by this reference.

BACKGROUND OF THE INVENTION

1. Field of the Invention

The present invention relates to a substrate structure in which a mounted component is disposed between substrates arranged side by side.

2. Description of the Related Art

Endoscopes are used in, e.g., medical fields and industrial fields. Examples of the endoscopes include what are called electronic endoscopes with an image pickup apparatus incorporated in a distal end portion of an insertion portion thereof. For the electronic endoscopes, there is a demand for image quality enhancement, and thus, e.g., an increase in number of pixels in image pickup devices is being pursued.

In the endoscopes, there is a long transmission passage connecting the image pickup apparatus incorporated in the distal end portion of the insertion portion and, for example, a video processor, which is an external apparatus. Therefore, a relay substrate that amplifies a drive signal for an image pickup device is provided inside the endoscope operation portion to enhance the image quality and reduce diameters of signal cables inserted inside the insertion portion.

Inside the endoscope operation portion, many incorporated endoscope components are inserted in addition to the signal cables. Examples of the incorporated endoscope components include, e.g., a light guide fiber bundle for supplying illuminating light, an air feeding tube included in an air feeding conduit, a water feeding tube included in a water feeding conduit, a dual-purpose tube that serves as a suction conduit and a treatment instrument conduit, and bending wires that make a bending portion perform a bending operation.

Figure 1:
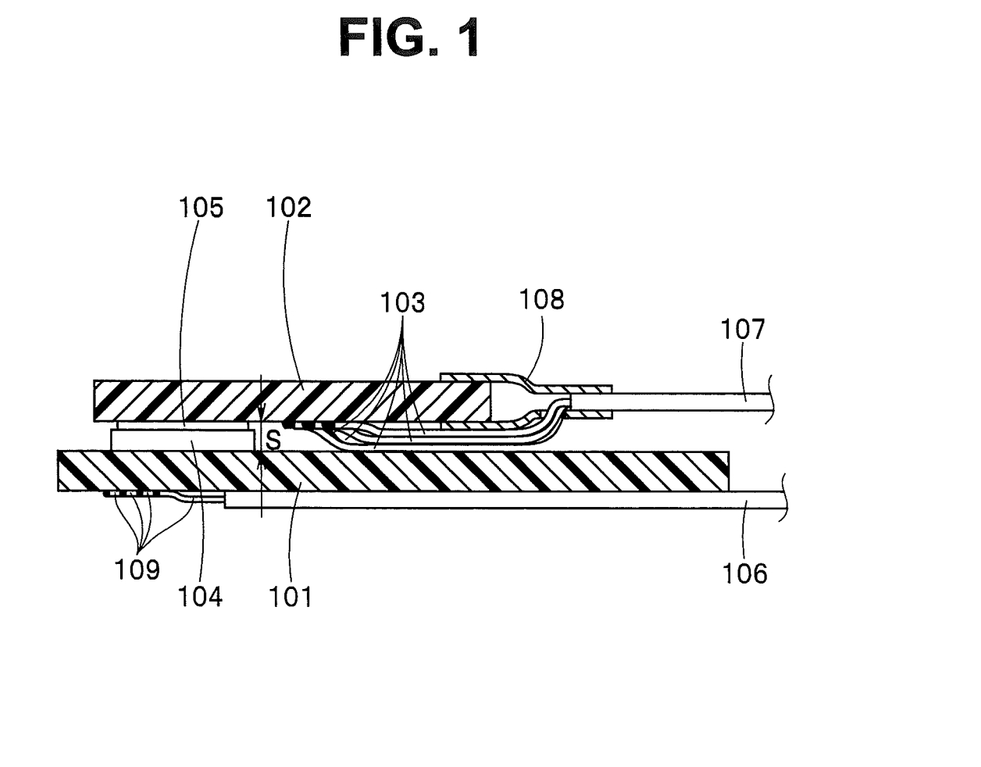
FIG. 1 is a diagram illustrating an example of a substrate structure.

Thus, the relay substrate is configured to have a small size. As a result, as illustrated in FIG. 1, a spacing between a first substrate 101 and a second substrate 102 included in a relay substrate is reduced. Then, it is necessary that a plurality of signal wires 103 be disposed in the reduced space S in such a manner that the plurality of signal wires 103 are prevented from electrical contact. However, a technique for disposing the plurality of signal wires 103 in the reduced space S requires a lot of skills.

Note that reference numeral 104 denotes a first connector mounted on the first substrate 101, reference numeral 105 denotes a second connector mounted on the second substrate 102, reference numeral 106 denotes a first signal cable, reference numeral 107 denotes a second signal cable, and reference numeral 108 denote a cable retainer member. The first signal cable 106 includes a plurality of signal wires 109 connected to connection portions (not illustrated) provided on the first substrate 101. The second signal cable 107 includes a plurality of signal wires 103 connected to connection portions (not illustrated) provided on the second substrate 102. The cable retainer member 108 is a member for attaching the second signal cable 107 to the second substrate 102.

Japanese Patent Application Laid-Open Publication No. 2009-158606 discloses a technique for forming an electronic device so that the electronic device can conform to high-density mounting and ensure an electromagnetic shielding effect.

SUMMARY OF THE INVENTION

A substrate structure according to an aspect of the present invention includes: a first substrate having stiffness; a second substrate including a front face disposed so as to face a front face of the first substrate, the second substrate having stiffness; a substrate spacing holding member provided between the front face of the first substrate and the front face of the second substrate facing each other, the substrate spacing holding member holding a spacing between the front faces of the two substrates at a predetermined value; a mounted component including a signal wire mounted on the second substrate, the signal wire projecting from the front face of the second substrate toward the front face of the first substrate, including an end portion electrically connected to the second substrate and extending from the substrate to an outside along the front face of the second substrate; a through hole provided in the first substrate, the through hole allowing a projecting part of the mounted component to be disposed therein; and a shielding member for electric shielding, the shielding member being provided on a back face side of the first substrate and covering an entirety or at least a part of an opening of the through hole.

DETAILED DESCRIPTION OF THE PREFERRED EMBODIMENT

An embodiment of the present invention will be described below with reference to the drawings.

Figure 2:
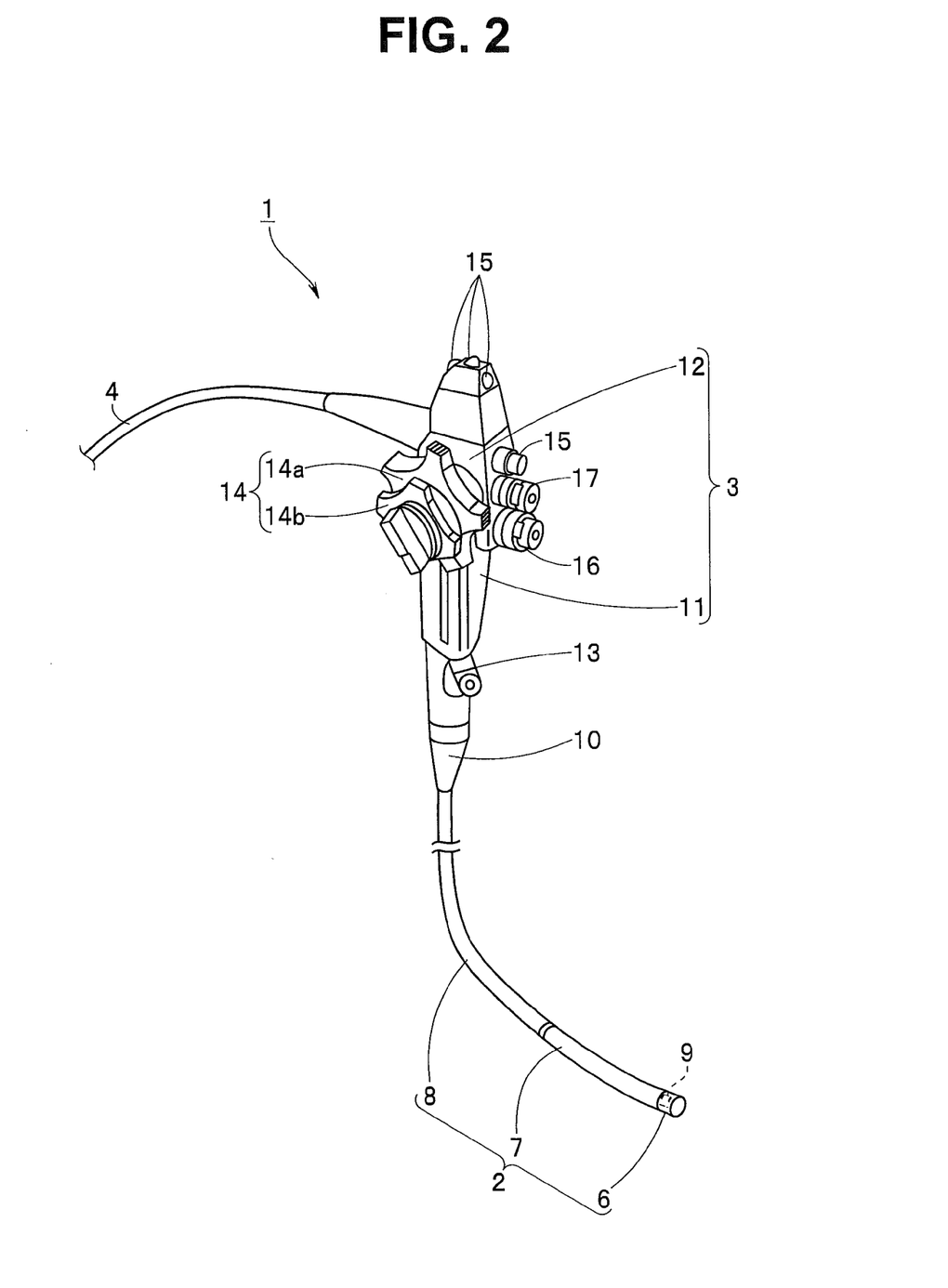
FIG. 2 is a diagram illustrating an endoscope according to the present embodiment.

As illustrated in FIG. 2, an endoscope 1 includes an insertion portion 2, an operation portion 3 and a universal cable 4. An endoscope connector (not illustrated) is provided at a proximal end portion of the universal cable 4. The endoscope connector is detachably connected to, for example, a camera control unit, which is an external apparatus.

The insertion portion 2 is an elongated member having a long length, which is to be inserted to a site to be observed. The insertion portion 2 includes a distal end portion 6, a bending portion 7 and a flexible tube portion 8, which are continuously provided. In the distal end portion 6, an illumination optical system that includes a light guide (not illustrated) and an image pickup apparatus including an image pickup device 9 including, e.g., a CCD or C-MOS are incorporated. The bending portion 7 is configured so as to bend in, for example, four directions, upward, downward, rightward and leftward. The flexible tube portion 8 is a tubular member having a long length and flexibility.

The operation portion 3 includes a combination of a first sheathing body 11 and a second sheathing body 12. In the first sheathing body 11, for example, a treatment instrument insertion port 13 is provided. A proximal end portion of the insertion portion 2 is integrally joined and fixed to the distal end side of the first sheathing body 11 via a bend preventing member 10.

At the second sheathing body 12, e.g., a bending operation portion 14, various kinds of switches 15, an air/water feeding button 16 and a suction button 17 are provided. At the bending operation portion 14, for example, bending operation knobs 14*a* and 14*b* for performing a bending operation of the bending portion 7 are provided. A surgeon turns, for example, the bending operation knob 14*a* in a predetermined direction, whereby non-illustrated bending wires are pulled or loosened to bend the bending portion 7 upward.

Note that examples of the various kinds of switches 15 include, e.g., a release switch, a freeze switch and an observation mode selection switch for switching between normal observation and fluorescent observation.

Figure 3:
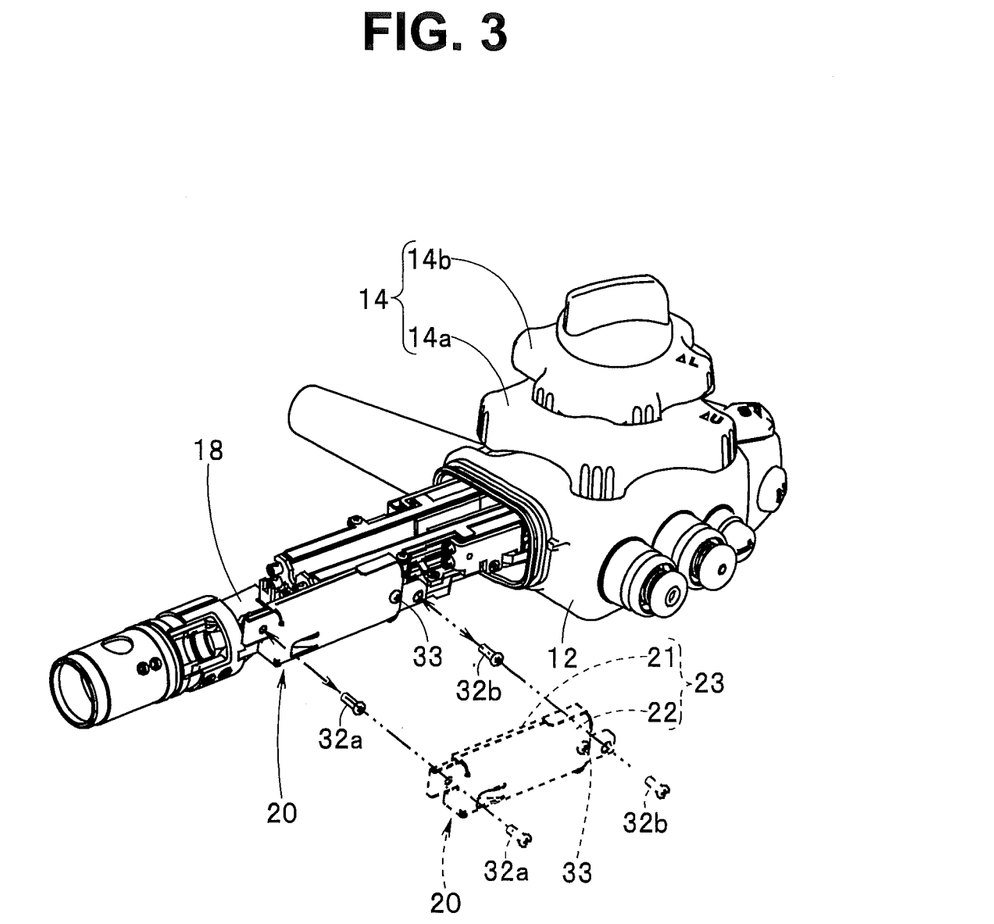
FIG. 3 is a diagram illustrating a relay unit provided inside an operation portion of the endoscope according to the present embodiment.

As illustrated in FIG. 3, a fixed plate 18, which is an operation portion framework component, is integrally fixed at a predetermined position in the second sheathing body 12 included in the operation portion 3. The fixed plate 18 includes, for example, a stainless steel. The fixed plate 18 is shaped so that various kinds of components provided in the operation portion 3 can be attached to the fixed plate 18 in an optimum manner.

Reference numeral 20 denotes a relay unit. The relay unit 20 includes a housing case 23 including a case body 21 and a cover body 22. The housing case 23 is detachably attached to a predetermined position in the fixed plate 18 via attachment screws 32*a* and 32*b*.

Figure 4:
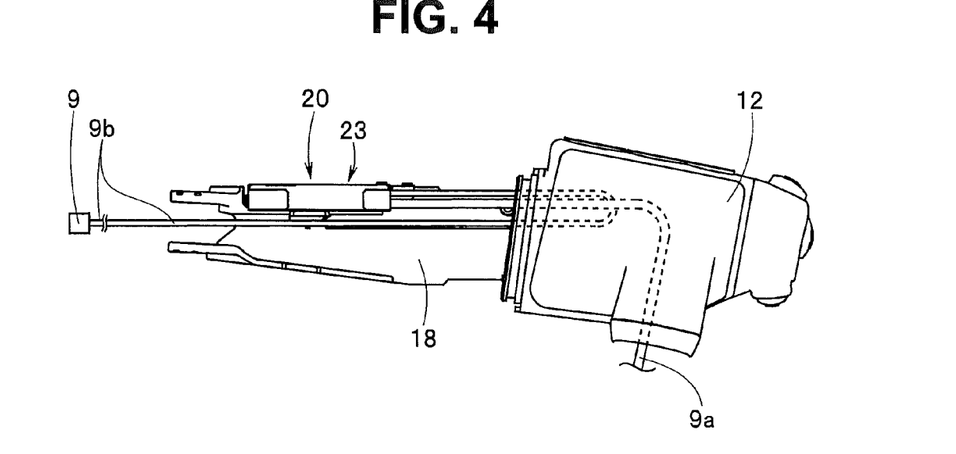
FIG. 4 is a diagram illustrating a relationship between the relay unit, and a first signal cable and a second signal cable.

As illustrated in FIG. 4, a first signal cable 9*a* and a second signal cable 9*b* are connected to the relay unit 20.

An end of the first signal cable 9*a* is connected to, for example, a substrate inside the endoscope connector. The other end of the first signal cable 9*a* is connected to a first drive signal relay substrate (reference numeral 24 in FIG. 5 and abbreviated as "first substrate"), which will be described later, inside the relay unit 20.

The second signal cable 9*b* extends from the image pickup device 9 provided in the insertion portion 2. An end of the second signal cable 9*b* is connected to the image pickup device 9. The other end of the second signal cable 9*b* is connected to a second drive signal relay substrate (reference numeral 25 in FIG. 5 and abbreviated as "second substrate"), which will be described later, inside the relay unit 20.

In a state in which the relay unit 20 is attached and fixed to the fixed plate 18, the first signal cable 9*a* and the second signal cable 9*b* thrust into the housing case 23 from the proximal end face side of the relay unit 20.

Here, an example of the substrate structure will be described.

Figure 5:
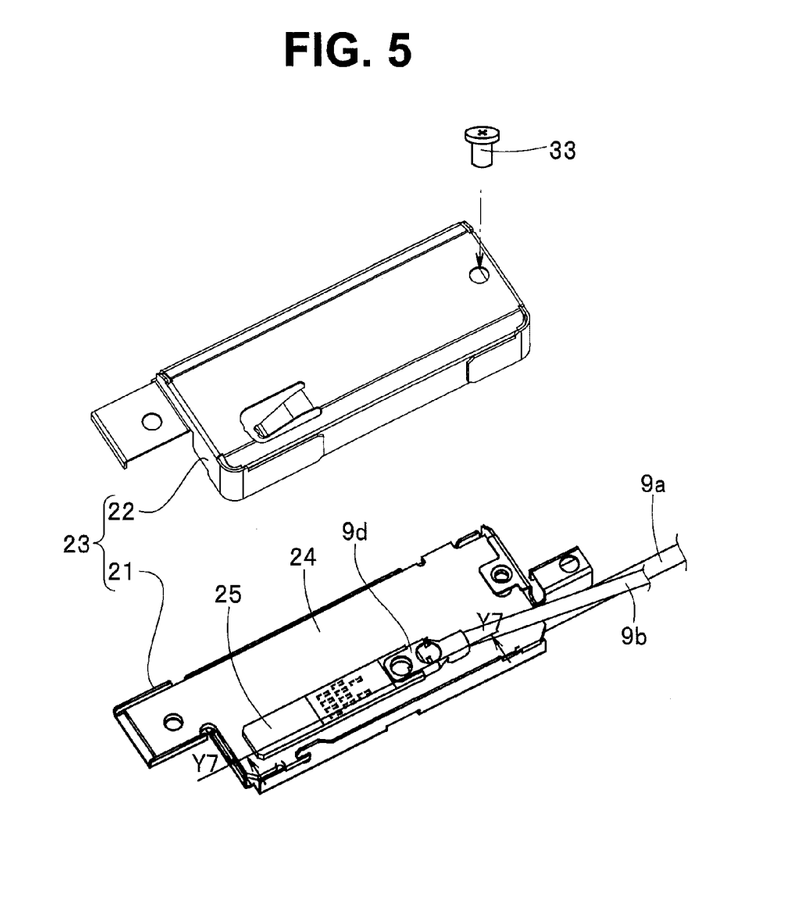
FIG. 5 is a diagram illustrating a configuration of a housing case, and, e.g., a first substrate, a second substrate, the first signal cable and the second signal cable arranged in an inner space of a case body.

As illustrated in FIGS. 3 and 5, the housing case 23 includes the case body 21 and the cover body 22 integrally fixed via a fixing screw 33. The housing case 23 is a shielding case. The case body 21 is configured in a box shape using a shielding member. The cover body 22 is also configured in a box shape using a shielding member. The cover body 22 occludes an opening of the case body 21.

As illustrated in FIG. 5, as a result of removing the fixing screw 33 from the housing case 23, the case body 21 and the cover body 22 are separated from each other in such a manner as illustrated in the Figure. In an inner space of the case body 21, e.g., the first substrate 24, the second substrate 25, the first signal cable 9*a* and the second signal cable 9*b* are arranged.

Figure 6:
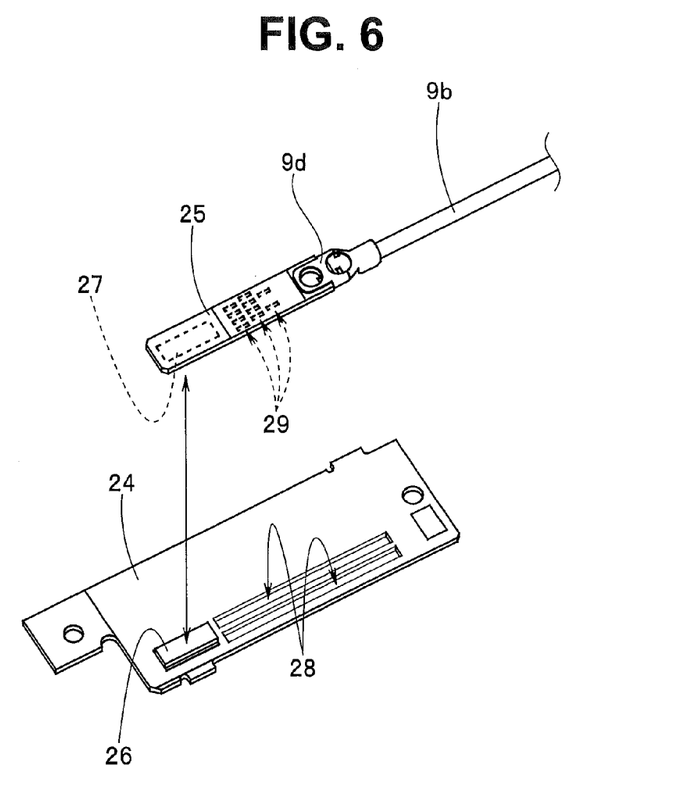
FIG. 6 is a diagram illustrating the first substrate and the second substrate.

As illustrated in FIG. 6, the first substrate 24 and the second substrate 25 are detachably attachable to each other.

A first connector 26 is mounted at a predetermined position on a front face, which is a surface of the first substrate 24. On a front face of the second substrate 25, a second connector 27, which is detachably attachable to the first connector 26, is mounted.

Figure 7:
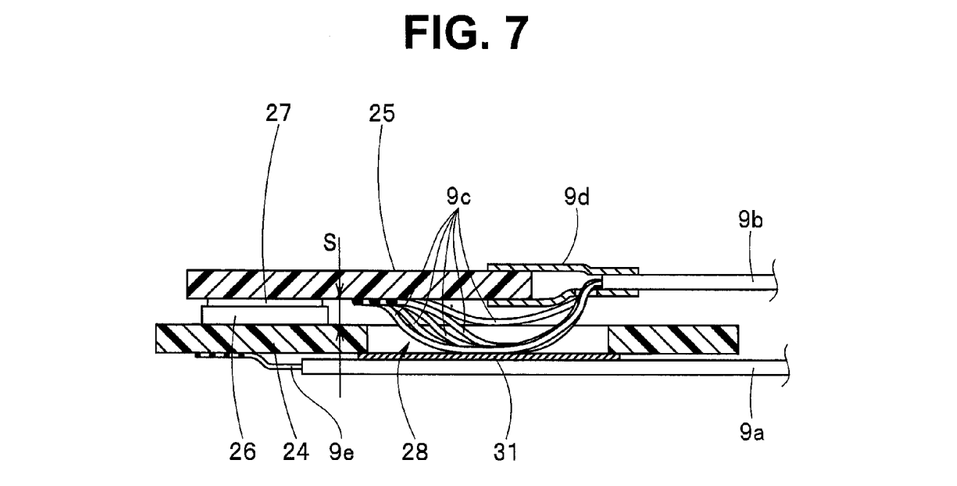
FIG. 7 is a diagram illustrating a state in which a first connector of the first substrate and a second connector of the second substrate are connected.

As illustrated in FIGS. 6 and 7, the second connector 27 is provided on one short side of the second substrate 25. A plurality of (for example, ten) signal wire connection portions 29 are provided at predetermined positions on the other short side relative to the second connector 27 on the front face of the second substrate 25.

Respective signal wires 9*c* inserted through the second signal cable 9*b* are connected to the signal wire connection portions 29. Each signal wire 9*c* with one end subjected to electrical connection extends from the substrate 25 to the outside along the front face of the second substrate 25. The signal wires 9*c* are mounted components.

Reference numeral 9*d* denotes a cable retainer member. The cable retainer member 9*d* is a member for positioning and fixing an end portion of the second signal cable 9*b* at an end portion on the other short side of the second substrate 25.

On the other hand, at predetermined positions in the first substrate 24, for example, two long holes 28, which are through holes, are formed side by side. Note that positions where the long holes 28 are formed and the number of the long holes 28 are set in consideration of positions where the respective signal wires 9*c* connected to the plurality of signal wire connection portions 29 provided on the front face of the second substrate 25 are disposed.

Long sides of the long holes 28 are parallel to long sides of the first substrate 24. Dimensions of short sides of the long holes 28 are set in consideration of a diameter and the number of the signal wires 9*c* and a thickness of the first substrate 24. In the present embodiment, the short sides are set to be 2.5 times the diameter of the signal wires 9*c* so that the four signal wires 9*c* can be received in each long hole 28.

Openings of the long holes 28 formed in a back face of the first substrate 24 are occluded by a shielding member 31 including a metal plate member having electrical conductivity. The shielding member 31 is connected to a shielding pattern provided on the first substrate 24. It is preferable that the entire openings of the long holes 28 be occluded by the shielding member 31. However, the long holes 28 may be partially occluded by the shielding member 31.

As illustrated in FIG. 7, the first connector 26 of the first substrate 24 and the second connector 27 of the second substrate 25 are arranged side by side in a predetermined spacing. In other words, in the present embodiment, the first connector 26 and the second connector 27 provide a substrate spacing holding member that sets and holds a spacing between the front faces of the two substrates 24 and 25 to a space S providing a predetermined distance.

In the present embodiment, in a state in which the first connector 26 of the first substrate 24 and the second connector 27 of the second substrate 25 are connected, the front face of the first substrate 24 and the front face of the second substrate 25 face each other with the space S therebetween. The long holes 28 are formed in the first substrate 24.

When a worker performs the work for connecting the first substrate 24 and the second substrate 25, the worker disposes four signal wires 9c from among the ten signal wires 9c connected to the second substrate 25 in one long hole 28 so that the four signal wires 9c are received in the long hole 28. Then, the worker disposes four signal wires 9c from among the remaining six signal wires 9c in the other long hole 28 so that the four signal wires 9c are received in the other long hole 28. Then, the worker disposes the remaining two signal wires 9c on the front face of the first substrate 24.

As a result, the signal wires 9c are disposed without physical interference between the signal wires and the substrates 24 and 25.

Also, after the completion of the connection work, the worker occludes the openings of the long holes 28 on the back face side of the first substrate 24 using the shielding member 31. As a result, the signal wires 9c are prevented from being subject to electrical interference.

As described above, in a configuration in which two substrates 24 and 25 are disposed side by side, long holes 28 that allow signal wires 9c provided on a front face of the second substrate 25 and projecting toward a front face of the first substrate 24 to be received and disposed therein are provided in the first substrate 24, and openings of the long holes 28 on the back face side of the first substrate 24 are occluded by a shielding member 31.

This configuration enables prevention of the trouble of physical interference between the signal wires 9c and the substrates 24 and 25 and the trouble of the signal wire 9c being subject to electrical interference, in addition to reduction in substrate spacing.

Figure 8:
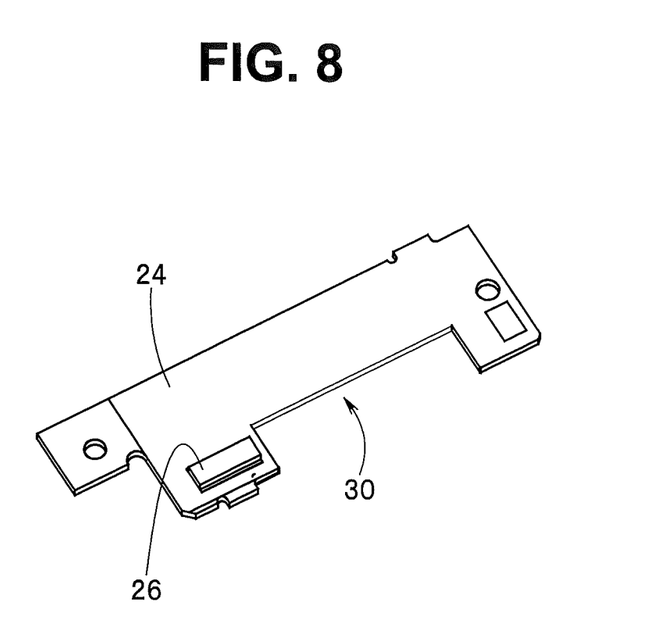
FIG. 8 is a diagram illustrating a first substrate including a cutout.

Note that, in the above-described embodiment, the long holes 28 are provided in the first substrate 24. However, instead of the long holes 28, a cutout 30, which is illustrated in FIG. 8, may be provided as a through hole.

Also, in the above-described embodiment, the signal wires 9c are provided as mounted components. However, the mounted components are not limited to the signal wires 9c and may be, e.g., electronic components.

Also, in the above-described embodiment, two signal wires 9c are arranged on the front face of the first substrate 24. However, a configuration that enables five signal wires 9c to be received and disposed in each long hole 28 may be employed. This configuration requires no signal wires 9c to be disposed on the front face of the first substrate 24, enabling further reduction of the space S.

Also, in the above-described embodiment, the first connector 26 and the second connector 27 provide a substrate spacing holding member. However, so-called spacer(s) may be provided as the substrate spacing holding member: one spacer may be provided on one of substrates, a plurality of spacers may be provided on one of substrates or a spacer may be provided on each of two substrates.

Also, electronic components are mounted on at least one of the first substrate 24 and the second substrate 25 to amplify a drive signal for the image pickup device 9 in order to overcome signal deterioration such as attenuation and/or dullness.

Also, the signal wires 9e inserted through the first signal cable 9a are connected to a plurality of signal wire connection portions (not illustrated) provided on the back face of the first substrate 25.

The above-described substrate structure is not limited to ones provided in operation portions of endoscopes, and may be ones arranged in, e.g., portable electronic devices.

The present invention is not limited only to the above-described embodiment, and various modifications are possible without departing from the spirit of the invention.

What is claimed is:

1. A substrate structure comprising:
a first substrate having stiffness;
a second substrate including a front face disposed so as to face a front face of the first substrate, the second substrate having stiffness;
a substrate spacing holding member provided between the front face of the first substrate and the front face of the second substrate facing each other, the substrate spacing holding member holding a spacing between the front faces of the two substrates at a predetermined value;
a mounted component including a signal wire mounted on the second substrate, the signal wire projecting from the front face of the second substrate toward the front face of the first substrate, including an end portion electrically connected to the second substrate and extending from the substrate to an outside along the front face of the second substrate;
a through hole provided in the first substrate, the through hole allowing a projecting part of the mounted component to be disposed therein; and
a shielding member for electric shielding, the shielding member being provided on a back face side of the first substrate and covering an entirety or at least a part of an opening of the through hole.

2. The substrate structure according to claim 1, wherein the substrate spacing holding member includes joining members disposed in a vicinity of the mounted component projecting from the front face of the second substrate and a vicinity of the through hole formed in the first substrate, respectively, the joining members joining the first substrate and the second substrate.

3. The substrate structure according to claim 2, wherein the joining members include connectors connecting the first substrate and the second substrate.

4. The substrate structure according to claim 1, wherein the shielding member includes a metal plate detachably provided on the first substrate.

5. The substrate structure according to claim 1, wherein the first substrate and the second substrate are provided inside an operation portion of an endoscope.

* * * * *